United States Patent
Liu et al.

(10) Patent No.: US 6,222,028 B1
(45) Date of Patent: Apr. 24, 2001

(54) **POLYNUCLEOTIDES ENCODING CELLULASE ENZYMES FROM *PIROMYCES RHIZINFLATA***

(75) Inventors: Jin-Hao Liu, Calgary; Kuo-Joan Cheng, Richmond, both of (CA); Cheng-Fang Tsai, Taipei Hsien; Chia-Chieh Chang, Taipei, both of (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/419,459

(22) Filed: Oct. 15, 1999

(51) Int. Cl.[7] .................................................. C07H 21/04
(52) U.S. Cl. ......................................... 536/23.2; 536/23.1
(58) Field of Search ........................ 536/23.2; 435/320.1, 435/252.3, 410

(56) References Cited

U.S. PATENT DOCUMENTS

| | | |
|---|---|---|
| 4,894,338 | 1/1990 | Knowles et al. .................. 435/172.3 |
| 5,047,332 | 9/1991 | Chahal .................................. 435/42 |
| 5,120,463 | 6/1992 | Bjork et al. ...................... 252/174.12 |
| 5,432,074 | 7/1995 | Evans et al. .......................... 435/200 |
| 5,688,290 | 11/1997 | Bjork et al. ............................. 8/401 |
| 5,700,686 | 12/1997 | Foody et al. ......................... 435/263 |

OTHER PUBLICATIONS

Xue et al. A novel polysaccharide hydrolase cDNA (celD) from neocallimastix patricarum encoding three multi–functional catalytic domains with with endoglucanase, cellobiohydrolase and xylanase activities. J. of General Microbiology (1992) 138:2397–2403.*
GenBank Accession No. AF053363, Mar. 1998.*
Fujino et al. Cloning, Sequencing, and Expression of an Endoglucanase Gene from the Rumen Anaerobic Fungus Neocallimastix frontalis MCH3. Bioscience, Blotechnology, and Biochemistry 62(9):1795–1798, Sep. 1998.*

* cited by examiner

*Primary Examiner*—Ponnathapu Achutamurthy
*Assistant Examiner*—Kathleen Kerr
(74) *Attorney, Agent, or Firm*—Fish & Richardson P.C.

(57) ABSTRACT

The invention relates to a cellulase enzyme, elgA, isolated from the fungus *Piromyces rhizinflata* and nucleic acids encoding it.

3 Claims, No Drawings

SEQUENCE LISTING

<160> NUMBER OF SEQ ID NOS: 10

<210> SEQ ID NO 1
<211> LENGTH: 2110
<212> TYPE: DNA
<213> ORGANISM: Piromyces rhizinflata
<220> FEATURE:
<221> NAME/KEY: CDS
<222> LOCATION: (3)...(1749)

<400> SEQUENCE: 1

```
gg cac gag ctt gaa tgg aac att aat tta atg aag aaa aga ttt gtt        47
   His Glu Leu Glu Trp Asn Ile Asn Leu Met Lys Lys Arg Phe Val
   1               5                  10                  15 gat caa ggt att cca atg att ctt ggt gaa tat ggt gct atg aac cgt        95
Asp Gln Gly Ile Pro Met Ile Leu Gly Glu Tyr Gly Ala Met Asn Arg
                20                  25                  30 gac aat gaa gaa gat cgt gct act tgg gct gaa ttc tac atg gaa aag       143
Asp Asn Glu Glu Asp Arg Ala Thr Trp Ala Glu Phe Tyr Met Glu Lys
            35                  40                  45 gtt act gct atg gga gtt cca caa atc tgg tgg gat aat ggt atc ttc       191
Val Thr Ala Met Gly Val Pro Gln Ile Trp Trp Asp Asn Gly Ile Phe
        50                  55                  60 caa ggt act ggt gaa cgt ttt ggt ctt ctt gat cgt aag aac tta aag       239
Gln Gly Thr Gly Glu Arg Phe Gly Leu Leu Asp Arg Lys Asn Leu Lys
    65                  70                  75 att gtt tat cca act att gtt gct gct tta caa aag ggt aga ggt tta       287
Ile Val Tyr Pro Thr Ile Val Ala Ala Leu Gln Lys Gly Arg Gly Leu
80                  85                  90                  95 gaa gtt aat gtt gtt cat gct gtt gaa aaa aaa cca gac gaa cca act       335
Glu Val Asn Val Val His Ala Val Glu Lys Lys Pro Asp Glu Pro Thr
                100                 105                 110 aaa act acc aaa cca act gaa cca act gaa act act agt cca gaa gaa       383
Lys Thr Thr Lys Pro Thr Glu Pro Thr Glu Thr Thr Ser Pro Glu Glu
            115                 120                 125 tca act aag cca gaa gaa cca act ggt aat atc cgt gat att tca tca       431
Ser Thr Lys Pro Glu Glu Pro Thr Gly Asn Ile Arg Asp Ile Ser Ser
        130                 135                 140 aag gaa ttg att aag gaa atg aat ttc ggt tgg aat tta ggt aat act       479
Lys Glu Leu Ile Lys Glu Met Asn Phe Gly Trp Asn Leu Gly Asn Thr
    145                 150                 155
```

-continued

```
atg gat gct caa tgt att gaa tac tta aat tat gaa aag gat caa act         527
Met Asp Ala Gln Cys Ile Glu Tyr Leu Asn Tyr Glu Lys Asp Gln Thr
160                 165                 170                 175 gct tca gaa act tgc tgg ggt aat cca aag act act gaa gat atg ttc         575
Ala Ser Glu Thr Cys Trp Gly Asn Pro Lys Thr Thr Glu Asp Met Phe
            180                 185                 190 aag gtt tta atc gac aac caa ttt aat gtc ttc cgt att cca act act         623
Lys Val Leu Ile Asp Asn Gln Phe Asn Val Phe Arg Ile Pro Thr Thr
                195                 200                 205 tgg tct ggt cac ttc ggt gaa gct cca gat tat aag att gat gaa aaa         671
Trp Ser Gly His Phe Gly Glu Ala Pro Asp Tyr Lys Ile Asp Glu Lys
        210                 215                 220 tgg tta aag aga gtt cat gaa gtt gtt gat tat cca tac aag aac gga         719
Trp Leu Lys Arg Val His Glu Val Val Asp Tyr Pro Tyr Lys Asn Gly
    225                 230                 235 gca ttt gtt atc tta aat ctt cat cat gaa acc tgg aat cat gcc ttc         767
Ala Phe Val Ile Leu Asn Leu His His Glu Thr Trp Asn His Ala Phe
240                 245                 250                 255 tct gaa act ctt gat aca gcc aag gaa att tta gaa aag atc tgg tct         815
Ser Glu Thr Leu Asp Thr Ala Lys Glu Ile Leu Glu Lys Ile Trp Ser
            260                 265                 270 caa att gct gaa gaa ttt aag gat tat gat gaa cac tta atc ttc gaa         863
Gln Ile Ala Glu Glu Phe Lys Asp Tyr Asp Glu His Leu Ile Phe Glu
                275                 280                 285 gga tta aac gaa cca aga aag aat gat act cca gtt gaa tgg act ggt         911
Gly Leu Asn Glu Pro Arg Lys Asn Asp Thr Pro Val Glu Trp Thr Gly
        290                 295                 300 ggt gat caa gaa ggt tgg gat gct gtt aat gct atg aat gct gtt ttc         959
Gly Asp Gln Glu Gly Trp Asp Ala Val Asn Ala Met Asn Ala Val Phe
305                 310                 315 tta aag act gtt cgt agt gct ggt ggt aat aat cca aag cgt cat ctt        1007
Leu Lys Thr Val Arg Ser Ala Gly Gly Asn Asn Pro Lys Arg His Leu
320                 325                 330                 335 atg att cca cca tat gct gct gct tgt aat gaa aac tca ttc aac aac        1055
Met Ile Pro Pro Tyr Ala Ala Ala Cys Asn Glu Asn Ser Phe Asn Asn
            340                 345                 350 ttt atc ttc cca gaa gat gat gat aag gtt att gct tct gtt cat gcc        1103
Phe Ile Phe Pro Glu Asp Asp Asp Lys Val Ile Ala Ser Val His Ala
                355                 360                 365 tat gct cca tac aac ttt gcc tta aat aac ggt gaa gga gct gtt gat        1151
Tyr Ala Pro Tyr Asn Phe Ala Leu Asn Asn Gly Glu Gly Ala Val Asp
        370                 375                 380 aag ttt gat gca gct ggt aag aga gat ctt gaa tgg aac att aat tta        1199
Lys Phe Asp Ala Ala Gly Lys Arg Asp Leu Glu Trp Asn Ile Asn Leu
385                 390                 395 atg aag aag aga ttt gtt gat caa ggt att cca atg att ctt ggt gaa        1247
Met Lys Lys Arg Phe Val Asp Gln Gly Ile Pro Met Ile Leu Gly Glu
400                 405                 410                 415 tat ggt gct atg aac cgt gac aat gaa gaa gat cgt gct act tgg gct        1295
Tyr Gly Ala Met Asn Arg Asp Asn Glu Glu Asp Arg Ala Thr Trp Ala
            420                 425                 430 gaa ttc tac atg gaa aag gtt act gct atg gga gtt cca caa atc tgg        1343
Glu Phe Tyr Met Glu Lys Val Thr Ala Met Gly Val Pro Gln Ile Trp
                435                 440                 445 tgg gat aat ggt gtc ttc gaa ggt act ggt gaa cgt ttt ggt ctt ctt        1391
Trp Asp Asn Gly Val Phe Glu Gly Thr Gly Glu Arg Phe Gly Leu Leu
        450                 455                 460 gat cgt aag aac tta aag att gtt tat cca act att gtt gct gct tta        1439
Asp Arg Lys Asn Leu Lys Ile Val Tyr Pro Thr Ile Val Ala Ala Leu
465                 470                 475
```

-continued

| | |
|---|---|
| caa aag ggt aga ggt tta gaa gtt aat gtt gtt cat gct att gaa aaa<br>Gln Lys Gly Arg Gly Leu Glu Val Asn Val Val His Ala Ile Glu Lys<br>480                        485                    490                    495 | 1487 |
| gaa aca gag gaa tgt tgg tcc gaa aag tat ggt tat gaa tgt tgt tca<br>Glu Thr Glu Glu Cys Trp Ser Glu Lys Tyr Gly Tyr Glu Cys Cys Ser<br>                    500                    505                    510 | 1535 |
| cca aac aat act aag gtt gta gtc agt gat gaa agt ggt aaa tgg ggt<br>Pro Asn Asn Thr Lys Val Val Val Ser Asp Glu Ser Gly Lys Trp Gly<br>                515                    520                    525 | 1583 |
| gtt gaa aat ggt aac tgg tgt ggt gta ctc aaa tac act gaa act tgt<br>Val Glu Asn Gly Asn Trp Cys Gly Val Leu Lys Tyr Thr Glu Thr Cys<br>530                        535                    540 | 1631 |
| tgg tca ctt cca ttt gga tac cca tgt tgt cca cat tgt aag gct ctt<br>Trp Ser Leu Pro Phe Gly Tyr Pro Cys Cys Pro His Cys Lys Ala Leu<br>      545                    550                    555 | 1679 |
| act aag gat gag aat ggt aaa tgg gga gaa tta aat gga gaa tgg tat<br>Thr Lys Asp Glu Asn Gly Lys Trp Gly Glu Leu Asn Gly Glu Trp Tyr<br>560                        565                    570                    575 | 1727 |
| ggt att gtt gct gat aaa tgt t aaattataaa ataagaataa ataaatttct<br>Gly Ile Val Ala Asp Lys Cys<br>                    580 | 1779 |
| aatgaaaaat tatttaaaaa aaaataaaat agaaaaattt atatacacat atttctaata | 1839 |
| aaatgtcatt taaaattttt atttcttatt attttaata aaaaaaatta taagaaaaga | 1899 |
| aaatataaaa aataataata atgaatgaaa taaaatttta attatttatt cttttactta | 1959 |
| aagcaaaaaa aagaatttaa ttaaaatcaa gaatttttaa agatggaata tgtattttaa | 2019 |
| ataatagcta ataagattat aaaaattgtg taaaaatttt taaataaaat aaaaataaaa | 2079 |
| taaataaata aataaataaa aaaaaaata a | 2110 |

<210> SEQ ID NO 2
<211> LENGTH: 582
<212> TYPE: PRT
<213> ORGANISM: Piromyces rhizinflata

<400> SEQUENCE: 2

His Glu Leu Glu Trp Asn Ile Asn Leu Met Lys Lys Arg Phe Val Asp
1               5                   10               15

Gln Gly Ile Pro Met Ile Leu Gly Glu Tyr Gly Ala Met Asn Arg Asp
               20                   25               30

Asn Glu Glu Asp Arg Ala Thr Trp Ala Glu Phe Tyr Met Glu Lys Val
           35                   40               45

Thr Ala Met Gly Val Pro Gln Ile Trp Trp Asp Asn Gly Ile Phe Gln
50                    55                   60

Gly Thr Gly Glu Arg Phe Gly Leu Leu Asp Arg Lys Asn Leu Lys Ile
65               70                   75               80

Val Tyr Pro Thr Ile Val Ala Ala Leu Gln Lys Gly Arg Gly Leu Glu
                    85                   90               95

Val Asn Val Val His Ala Val Glu Lys Lys Pro Asp Glu Pro Thr Lys
           100                  105               110

Thr Thr Lys Pro Thr Glu Pro Thr Glu Thr Thr Ser Pro Glu Glu Ser
        115                  120               125

Thr Lys Pro Glu Glu Pro Thr Gly Asn Ile Arg Asp Ile Ser Ser Lys
    130                    135                  140

Glu Leu Ile Lys Glu Met Asn Phe Gly Trp Asn Leu Gly Asn Thr Met
145                 150                   155               160

-continued

Asp Ala Gln Cys Ile Glu Tyr Leu Asn Tyr Glu Lys Asp Gln Thr Ala
                165                 170                 175

Ser Glu Thr Cys Trp Gly Asn Pro Lys Thr Thr Glu Asp Met Phe Lys
                180                 185                 190

Val Leu Ile Asp Asn Gln Phe Asn Val Phe Arg Ile Pro Thr Thr Trp
                195                 200                 205

Ser Gly His Phe Gly Glu Ala Pro Asp Tyr Lys Ile Asp Glu Lys Trp
                210                 215                 220

Leu Lys Arg Val His Glu Val Val Asp Tyr Pro Tyr Lys Asn Gly Ala
225                 230                 235                 240

Phe Val Ile Leu Asn Leu His His Glu Thr Trp Asn His Ala Phe Ser
                245                 250                 255

Glu Thr Leu Asp Thr Ala Lys Glu Ile Leu Glu Lys Ile Trp Ser Gln
                260                 265                 270

Ile Ala Glu Glu Phe Lys Asp Tyr Asp Glu His Leu Ile Phe Glu Gly
                275                 280                 285

Leu Asn Glu Pro Arg Lys Asn Asp Thr Pro Val Glu Trp Thr Gly Gly
                290                 295                 300

Asp Gln Glu Gly Trp Asp Ala Val Asn Ala Met Asn Ala Val Phe Leu
305                 310                 315                 320

Lys Thr Val Arg Ser Ala Gly Gly Asn Asn Pro Lys Arg His Leu Met
                325                 330                 335

Ile Pro Pro Tyr Ala Ala Ala Cys Asn Glu Asn Ser Phe Asn Asn Phe
                340                 345                 350

Ile Phe Pro Glu Asp Asp Lys Val Ile Ala Ser Val His Ala Tyr
                355                 360                 365

Ala Pro Tyr Asn Phe Ala Leu Asn Asn Gly Glu Gly Ala Val Asp Lys
                370                 375                 380

Phe Asp Ala Ala Gly Lys Arg Asp Leu Glu Trp Asn Ile Asn Leu Met
385                 390                 395                 400

Lys Lys Arg Phe Val Asp Gln Gly Ile Pro Met Ile Leu Gly Glu Tyr
                405                 410                 415

Gly Ala Met Asn Arg Asp Asn Glu Glu Asp Arg Ala Thr Trp Ala Glu
                420                 425                 430

Phe Tyr Met Glu Lys Val Thr Ala Met Gly Val Pro Gln Ile Trp Trp
                435                 440                 445

Asp Asn Gly Val Phe Glu Gly Thr Gly Glu Arg Phe Gly Leu Leu Asp
                450                 455                 460

Arg Lys Asn Leu Lys Ile Val Tyr Pro Thr Ile Val Ala Ala Leu Gln
465                 470                 475                 480

Lys Gly Arg Gly Leu Glu Val Asn Val His Ala Ile Glu Lys Glu
                485                 490                 495

Thr Glu Glu Cys Trp Ser Glu Lys Tyr Gly Tyr Glu Cys Cys Ser Pro
                500                 505                 510

Asn Asn Thr Lys Val Val Val Ser Asp Glu Ser Gly Lys Trp Gly Val
                515                 520                 525

Glu Asn Gly Asn Trp Cys Gly Val Leu Lys Tyr Thr Glu Thr Cys Trp
                530                 535                 540

Ser Leu Pro Phe Gly Tyr Pro Cys Cys Pro His Cys Lys Ala Leu Thr
545                 550                 555                 560

```
Lys Asp Glu Asn Gly Lys Trp Gly Glu Leu Asn Gly Glu Trp Tyr Gly
                565                 570                 575
Ile Val Ala Asp Lys Cys
        580

<210> SEQ ID NO 3
<211> LENGTH: 1170
<212> TYPE: DNA
<213> ORGANISM: Piromyces rhizinflata
<220> FEATURE:
<221> NAME/KEY: CDS
<222> LOCATION: (1)...(1170)

<400> SEQUENCE: 3 cca act aaa act acc aaa cca act gaa cca act gaa act act agt cca        48
Pro Thr Lys Thr Thr Lys Pro Thr Glu Pro Thr Glu Thr Thr Ser Pro
 1               5                  10                  15 gaa gaa tca act aag cca gaa gaa cca act ggt aat atc cgt gat att        96
Glu Glu Ser Thr Lys Pro Glu Glu Pro Thr Gly Asn Ile Arg Asp Ile
             20                  25                  30 tca tca aag gaa ttg att aag gaa atg aat ttc ggt tgg aat tta ggt       144
Ser Ser Lys Glu Leu Ile Lys Glu Met Asn Phe Gly Trp Asn Leu Gly
         35                  40                  45 aat act atg gat gct caa tgt att gaa tac tta aat tat gaa aag gat       192
Asn Thr Met Asp Ala Gln Cys Ile Glu Tyr Leu Asn Tyr Glu Lys Asp
     50                  55                  60 caa act gct tca gaa act tgc tgg ggt aat cca aag act act gaa gat       240
Gln Thr Ala Ser Glu Thr Cys Trp Gly Asn Pro Lys Thr Thr Glu Asp
 65                  70                  75                  80 atg ttc aag gtt tta atc gac aac caa ttt aat gtc ttc cgt att cca       288
Met Phe Lys Val Leu Ile Asp Asn Gln Phe Asn Val Phe Arg Ile Pro
                 85                  90                  95 act act tgg tct ggt cac ttc ggt gaa gct cca gat tat aag att gat       336
Thr Thr Trp Ser Gly His Phe Gly Glu Ala Pro Asp Tyr Lys Ile Asp
            100                 105                 110 gaa aaa tgg tta aag aga gtt cat gaa gtt gtt gat tat cca tac aag       384
Glu Lys Trp Leu Lys Arg Val His Glu Val Val Asp Tyr Pro Tyr Lys
        115                 120                 125 aac gga gca ttt gtt atc tta aat ctt cat cat gaa acc tgg aat cat       432
Asn Gly Ala Phe Val Ile Leu Asn Leu His His Glu Thr Trp Asn His
    130                 135                 140 gcc ttc tct gaa act ctt gat aca gcc aag gaa att tta gaa aag atc       480
Ala Phe Ser Glu Thr Leu Asp Thr Ala Lys Glu Ile Leu Glu Lys Ile
145                 150                 155                 160 tgg tct caa att gct gaa gaa ttt aag gat tat gat gaa cac tta atc       528
Trp Ser Gln Ile Ala Glu Glu Phe Lys Asp Tyr Asp Glu His Leu Ile
                165                 170                 175 ttc gaa gga tta aac gaa cca aga aag aat gat act cca gtt gaa tgg       576
Phe Glu Gly Leu Asn Glu Pro Arg Lys Asn Asp Thr Pro Val Glu Trp
            180                 185                 190 act ggt ggt gat caa gaa ggt tgg gat gct gtt aat gct atg aat gct       624
Thr Gly Gly Asp Gln Glu Gly Trp Asp Ala Val Asn Ala Met Asn Ala
        195                 200                 205 gtt ttc tta aag act gtt cgt agt gct ggt ggt aat aat cca aag cgt       672
Val Phe Leu Lys Thr Val Arg Ser Ala Gly Gly Asn Asn Pro Lys Arg
    210                 215                 220 cat ctt atg att cca cca tat gct gct gct tgt aat gaa aac tca ttc       720
His Leu Met Ile Pro Pro Tyr Ala Ala Ala Cys Asn Glu Asn Ser Phe
225                 230                 235                 240
```

```
aac aac ttt atc ttc cca gaa gat gat gat aag gtt att gct tct gtt    768
Asn Asn Phe Ile Phe Pro Glu Asp Asp Asp Lys Val Ile Ala Ser Val
            245                 250                 255 cat gcc tat gct cca tac aac ttt gcc tta aat aac ggt gaa gga gct    816
His Ala Tyr Ala Pro Tyr Asn Phe Ala Leu Asn Asn Gly Glu Gly Ala
        260                 265                 270 gtt gat aag ttt gat gca gct ggt aag aga gat ctt gaa tgg aac att    864
Val Asp Lys Phe Asp Ala Ala Gly Lys Arg Asp Leu Glu Trp Asn Ile
    275                 280                 285 aat tta atg aag aag aga ttt gtt gat caa ggt att cca atg att ctt    912
Asn Leu Met Lys Lys Arg Phe Val Asp Gln Gly Ile Pro Met Ile Leu
290                 295                 300 ggt gaa tat ggt gct atg aac cgt gac aat gaa gaa gat cgt gct act    960
Gly Glu Tyr Gly Ala Met Asn Arg Asp Asn Glu Glu Asp Arg Ala Thr
305                 310                 315                 320 tgg gct gaa ttc tac atg gaa aag gtt act gct atg gga gtt cca caa   1008
Trp Ala Glu Phe Tyr Met Glu Lys Val Thr Ala Met Gly Val Pro Gln
            325                 330                 335 atc tgg tgg gat aat ggt gtc ttc gaa ggt act ggt gaa cgt ttt ggt   1056
Ile Trp Trp Asp Asn Gly Val Phe Glu Gly Thr Gly Glu Arg Phe Gly
        340                 345                 350 ctt ctt gat cgt aag aac tta aag att gtt tat cca act att gtt gct   1104
Leu Leu Asp Arg Lys Asn Leu Lys Ile Val Tyr Pro Thr Ile Val Ala
    355                 360                 365 gct tta caa aag ggt aga ggt tta gaa gtt aat gtt gtt cat gct att   1152
Ala Leu Gln Lys Gly Arg Gly Leu Glu Val Asn Val Val His Ala Ile
370                 375                 380 gaa aaa gaa aca gag gaa                                           1170
Glu Lys Glu Thr Glu Glu
385                 390

<210> SEQ ID NO 4
<211> LENGTH: 390
<212> TYPE: PRT
<213> ORGANISM: Piromyces rhizinflata

<400> SEQUENCE: 4

Pro Thr Lys Thr Thr Lys Pro Thr Glu Pro Thr Glu Thr Thr Ser Pro
 1               5                  10                  15

Glu Glu Ser Thr Lys Pro Glu Glu Pro Thr Gly Asn Ile Arg Asp Ile
             20                  25                  30

Ser Ser Lys Glu Leu Ile Lys Glu Met Asn Phe Gly Trp Asn Leu Gly
         35                  40                  45

Asn Thr Met Asp Ala Gln Cys Ile Glu Tyr Leu Asn Tyr Glu Lys Asp
     50                  55                  60

Gln Thr Ala Ser Glu Thr Cys Trp Gly Asn Pro Lys Thr Thr Glu Asp
 65                  70                  75                  80

Met Phe Lys Val Leu Ile Asp Asn Gln Phe Asn Val Phe Arg Ile Pro
                 85                  90                  95

Thr Thr Trp Ser Gly His Phe Glu Ala Pro Asp Tyr Lys Ile Asp
            100                 105                 110

Glu Lys Trp Leu Lys Arg Val His Glu Val Val Asp Tyr Pro Tyr Lys
        115                 120                 125

Asn Gly Ala Phe Val Ile Leu Asn Leu His His Glu Thr Trp Asn His
    130                 135                 140

Ala Phe Ser Glu Thr Leu Asp Thr Ala Lys Glu Ile Leu Glu Lys Ile
145                 150                 155                 160
```

-continued

Trp Ser Gln Ile Ala Glu Glu Phe Lys Asp Tyr Asp Glu His Leu Ile
                165                 170                 175

Phe Glu Gly Leu Asn Glu Pro Arg Lys Asn Asp Thr Pro Val Glu Trp
            180                 185                 190

Thr Gly Gly Asp Gln Glu Gly Trp Asp Ala Val Asn Ala Met Asn Ala
        195                 200                 205

Val Phe Leu Lys Thr Val Arg Ser Ala Gly Gly Asn Asn Pro Lys Arg
    210                 215                 220

His Leu Met Ile Pro Pro Tyr Ala Ala Ala Cys Asn Glu Asn Ser Phe
225                 230                 235                 240

Asn Asn Phe Ile Phe Pro Glu Asp Asp Lys Val Ile Ala Ser Val
                245                 250                 255

His Ala Tyr Ala Pro Tyr Asn Phe Ala Leu Asn Asn Gly Glu Gly Ala
                260                 265                 270

Val Asp Lys Phe Asp Ala Ala Gly Lys Arg Asp Leu Glu Trp Asn Ile
            275                 280                 285

Asn Leu Met Lys Lys Arg Phe Val Asp Gln Gly Ile Pro Met Ile Leu
        290                 295                 300

Gly Glu Tyr Gly Ala Met Asn Arg Asp Asn Glu Gly Asp Arg Ala Thr
305                 310                 315                 320

Trp Ala Glu Phe Tyr Met Glu Lys Val Thr Ala Met Gly Val Pro Gln
                325                 330                 335

Ile Trp Trp Asp Asn Gly Val Phe Glu Gly Thr Gly Glu Arg Phe Gly
                340                 345                 350

Leu Leu Asp Arg Lys Asn Leu Lys Ile Val Tyr Pro Thr Ile Val Ala
            355                 360                 365

Ala Leu Gln Lys Gly Arg Gly Leu Glu Val Asn Val Val His Ala Ile
        370                 375                 380

Glu Lys Glu Thr Glu Glu
385                 390

<210> SEQ ID NO 5
<211> LENGTH: 109
<212> TYPE: PRT
<213> ORGANISM: Piromyces rhizinflata

<400> SEQUENCE: 5

His Glu Leu Glu Trp Asn Ile Asn Leu Met Lys Lys Arg Phe Val Asp
 1               5                  10                  15

Gln Gly Ile Pro Met Ile Leu Gly Glu Tyr Gly Ala Met Asn Arg Asp
                20                  25                  30

Asn Glu Glu Asp Arg Ala Thr Trp Ala Glu Phe Tyr Met Glu Lys Val
            35                  40                  45

Thr Ala Met Gly Val Pro Gln Ile Trp Trp Asp Asn Gly Ile Phe Gln
        50                  55                  60

Gly Thr Gly Glu Arg Phe Gly Leu Leu Asp Arg Lys Asn Leu Lys Ile
65                  70                  75                  80

Val Tyr Pro Thr Ile Val Ala Ala Leu Gln Lys Gly Arg Gly Leu Glu
                85                  90                  95

Val Asn Val Val His Ala Val Glu Lys Lys Pro Asp Glu
            100                 105

<210> SEQ ID NO 6
<211> LENGTH: 109
<212> TYPE: PRT
<213> ORGANISM: Piromyces rhizinflata -continued

```
<400> SEQUENCE: 6

Arg Asp Leu Glu Trp Asn Ile Asn Leu Met Lys Lys Arg Phe Val Asp
 1               5                  10                  15

Gln Gly Ile Pro Met Ile Leu Gly Glu Tyr Gly Ala Met Asn Arg Asp
            20                  25                  30

Asn Glu Glu Asp Arg Ala Thr Trp Ala Glu Phe Tyr Met Glu Lys Val
        35                  40                  45

Thr Ala Met Gly Val Pro Gln Ile Trp Trp Asp Asn Gly Val Phe Glu
    50                  55                  60

Gly Thr Gly Glu Arg Phe Gly Leu Leu Asp Arg Lys Asn Leu Lys Ile
 65                 70                  75                  80

Val Tyr Pro Thr Ile Val Ala Ala Leu Gln Lys Gly Arg Gly Leu Glu
                85                  90                  95

Val Asn Val Val His Ala Ile Glu Lys Glu Thr Glu Glu
            100                 105

<210> SEQ ID NO 7
<211> LENGTH: 42
<212> TYPE: DNA
<213> ORGANISM: Artificial Sequence
<220> FEATURE:
<221> NAME/KEY: misc_feature
<222> LOCATION: (1)...(42)
<223> OTHER INFORMATION: synthetically derived primer

<400> SEQUENCE: 7
gcaggatcca ttatggagct cccaactaaa actaccaaac ca                    42

<210> SEQ ID NO 8
<211> LENGTH: 39
<212> TYPE: DNA
<213> ORGANISM: Artificial Sequence
<220> FEATURE:
<221> NAME/KEY: misc_feature
<222> LOCATION: (1)...(39)
<223> OTHER INFORMATION: syntheticaly derived primer

<400> SEQUENCE: 8
ttcctcgagt tagagctctt cctctgtttc tttttcaat                        39

<210> SEQ ID NO 9
<211> LENGTH: 1182
<212> TYPE: DNA
<213> ORGANISM: Piromyces rhizinflata
<220> FEATURE:
<221> NAME/KEY: CDS
<222> LOCATION: (1)...(1182)

<400> SEQUENCE: 9 att atg gag ctc cca act aaa act acc aaa cca act gaa cca act gaa     48
Ile Met Glu Leu Pro Thr Lys Thr Thr Lys Pro Thr Glu Pro Thr Glu
 1               5                  10                  15 act act agt cca gaa gaa tca act aag cca gaa gaa cca act ggt aat     96
Thr Thr Ser Pro Glu Glu Ser Thr Lys Pro Glu Glu Pro Thr Gly Asn
            20                  25                  30 atc cgt gat att tca tca aag gaa ttg att aag gaa atg aat ttc ggt    144
Ile Arg Asp Ile Ser Ser Lys Glu Leu Ile Lys Glu Met Asn Phe Gly
        35                  40                  45 tgg aat tta ggt aat act atg gat gct caa tgt att gaa tac tta aat    192
Trp Asn Leu Gly Asn Thr Met Asp Ala Gln Cys Ile Glu Tyr Leu Asn
    50                  55                  60
```

-continued

| | |
|---|---|
| tat gaa aag gat caa act gct tca gaa act tgc tgg ggt aat cca aag<br>Tyr Glu Lys Asp Gln Thr Ala Ser Glu Thr Cys Trp Gly Asn Pro Lys<br>65                    70                    75                    80 | 240 |
| act act gaa gat atg ttc aag gtt tta atc gac aac caa ttt aat gtc<br>Thr Thr Glu Asp Met Phe Lys Val Leu Ile Asp Asn Gln Phe Asn Val<br>                   85                    90                    95 | 288 |
| ttc cgt att cca act act tgg tct ggt cac ttc ggt gaa gct cca gat<br>Phe Arg Ile Pro Thr Thr Trp Ser Gly His Phe Gly Glu Ala Pro Asp<br>              100                    105                    110 | 336 |
| tat aag att gat gaa aaa tgg tta aag aga gtt cat gaa gtt gtt gat<br>Tyr Lys Ile Asp Glu Lys Trp Leu Lys Arg Val His Glu Val Val Asp<br>              115                    120                    125 | 384 |
| tat cca tac aag aac gga gca ttt gtt atc tta aat ctt cat cat gaa<br>Tyr Pro Tyr Lys Asn Gly Ala Phe Val Ile Leu Asn Leu His His Glu<br>130                    135                    140 | 432 |
| acc tgg aat cat gcc ttc tct gaa act ctt gat aca gcc aag gaa att<br>Thr Trp Asn His Ala Phe Ser Glu Thr Leu Asp Thr Ala Lys Glu Ile<br>145                    150                    155                    160 | 480 |
| tta gaa aag atc tgg tct caa att gct gaa gaa ttt aag gat tat gat<br>Leu Glu Lys Ile Trp Ser Gln Ile Ala Glu Glu Phe Lys Asp Tyr Asp<br>                    165                    170                    175 | 528 |
| gaa cac tta atc ttc gaa gga tta aac gaa cca aga aag aat gat act<br>Glu His Leu Ile Phe Glu Gly Leu Asn Glu Pro Arg Lys Asn Asp Thr<br>              180                    185                    190 | 576 |
| cca gtt gaa tgg act ggt ggt gat caa gaa ggt tgg gat gct gtt aat<br>Pro Val Glu Trp Thr Gly Gly Asp Gln Glu Gly Trp Asp Ala Val Asn<br>                    195                    200                    205 | 624 |
| gct atg aat gct gtt ttc tta aag act gtt cgt agt gct ggt ggt aat<br>Ala Met Asn Ala Val Phe Leu Lys Thr Val Arg Ser Ala Gly Gly Asn<br>          210                    215                    220 | 672 |
| aat cca aag cgt cat ctt atg att cca cca tat gct gct gct tgt aat<br>Asn Pro Lys Arg His Leu Met Ile Pro Pro Tyr Ala Ala Ala Cys Asn<br>225                    230                    235                    240 | 720 |
| gaa aac tca ttc aac aac ttt atc ttc cca gaa gat gat gat aag gtt<br>Glu Asn Ser Phe Asn Asn Phe Ile Phe Pro Glu Asp Asp Asp Lys Val<br>                    245                    250                    255 | 768 |
| att gct tct gtt cat gcc tat gct cca tac aac ttt gcc tta aat aac<br>Ile Ala Ser Val His Ala Tyr Ala Pro Tyr Asn Phe Ala Leu Asn Asn<br>          260                    265                    270 | 816 |
| ggt gaa gga gct gtt gat aag ttt gat gca gct ggt aag aga gat ctt<br>Gly Glu Gly Ala Val Asp Lys Phe Asp Ala Ala Gly Lys Arg Asp Leu<br>              275                    280                    285 | 864 |
| gaa tgg aac att aat tta atg aag aag aga ttt gtt gat caa ggt att<br>Glu Trp Asn Ile Asn Leu Met Lys Lys Arg Phe Val Asp Gln Gly Ile<br>290                    295                    300 | 912 |
| cca atg att ctt ggt gaa tat ggt gct atg aac cgt gac aat gaa gaa<br>Pro Met Ile Leu Gly Glu Tyr Gly Ala Met Asn Arg Asp Asn Glu Glu<br>305                    310                    315                    320 | 960 |
| gat cgt gct act tgg gct gaa ttc tac atg gaa aag gtt act gct atg<br>Asp Arg Ala Thr Trp Ala Glu Phe Tyr Met Glu Lys Val Thr Ala Met<br>                    325                    330                    335 | 1008 |
| gga gtt cca caa atc tgg tgg gat aat ggt gtc ttc gaa ggt act ggt<br>Gly Val Pro Gln Ile Trp Trp Asp Asn Gly Val Phe Glu Gly Thr Gly<br>              340                    345                    350 | 1056 |
| gaa cgt ttt ggt ctt ctt gat cgt aag aac tta aag att gtt tat cca<br>Glu Arg Phe Gly Leu Leu Asp Arg Lys Asn Leu Lys Ile Val Tyr Pro<br>          355                    360                    365 | 1104 |
| act att gtt gct gct tta caa aag ggt aga ggt tta gaa gtt aat gtt<br>Thr Ile Val Ala Ala Leu Gln Lys Gly Arg Gly Leu Glu Val Asn Val<br>          370                    375                    380 | 1152 |

```
gtt cat gct att gaa aaa gaa aca gag gaa                                    1182
Val His Ala Ile Glu Lys Glu Thr Glu Glu
385             390
```

<210> SEQ ID NO 10
<211> LENGTH: 394
<212> TYPE: PRT
<213> ORGANISM: Piromyces rhizinflata

<400> SEQUENCE: 10

```
Ile Met Glu Leu Pro Thr Lys Thr Thr Lys Pro Thr Glu Pro Thr Glu
 1               5                  10                  15

Thr Thr Ser Pro Glu Glu Ser Thr Lys Pro Glu Glu Pro Thr Gly Asn
            20                  25                  30

Ile Arg Asp Ile Ser Ser Lys Glu Leu Ile Lys Glu Met Asn Phe Gly
        35                  40                  45

Trp Asn Leu Gly Asn Thr Met Asp Ala Gln Cys Ile Glu Tyr Leu Asn
    50                  55                  60

Tyr Glu Lys Asp Gln Thr Ala Ser Glu Thr Cys Trp Gly Asn Pro Lys
65                  70                  75                  80

Thr Thr Glu Asp Met Phe Lys Val Leu Ile Asp Asn Gln Phe Asn Val
                85                  90                  95

Phe Arg Ile Pro Thr Thr Trp Ser Gly His Phe Gly Glu Ala Pro Asp
            100                 105                 110

Tyr Lys Ile Asp Glu Lys Trp Leu Lys Arg Val His Glu Val Val Asp
        115                 120                 125

Tyr Pro Tyr Lys Asn Gly Ala Phe Val Ile Leu Asn Leu His His Glu
    130                 135                 140

Thr Trp Asn His Ala Phe Ser Glu Thr Leu Asp Thr Ala Lys Glu Ile
145                 150                 155                 160

Leu Glu Lys Ile Trp Ser Gln Ile Ala Glu Glu Phe Lys Asp Tyr Asp
                165                 170                 175

Glu His Leu Ile Phe Glu Gly Leu Asn Glu Pro Arg Lys Asn Asp Thr
            180                 185                 190

Pro Val Glu Trp Thr Gly Gly Asp Gln Glu Gly Trp Asp Ala Val Asn
        195                 200                 205

Ala Met Asn Ala Val Phe Leu Lys Thr Val Arg Ser Ala Gly Gly Asn
    210                 215                 220

Asn Pro Lys Arg His Leu Met Ile Pro Pro Tyr Ala Ala Ala Cys Asn
225                 230                 235                 240

Glu Asn Ser Phe Asn Asn Phe Ile Phe Pro Glu Asp Asp Lys Val
                245                 250                 255

Ile Ala Ser Val His Ala Tyr Ala Pro Tyr Asn Phe Ala Leu Asn Asn
            260                 265                 270

Gly Glu Gly Ala Val Asp Lys Phe Asp Ala Ala Gly Lys Arg Asp Leu
        275                 280                 285

Glu Trp Asn Ile Asn Leu Met Lys Lys Arg Phe Val Asp Gln Gly Ile
    290                 295                 300

Pro Met Ile Leu Gly Glu Tyr Gly Ala Met Asn Arg Asp Asn Glu Glu
305                 310                 315                 320

Asp Arg Ala Thr Trp Ala Glu Phe Tyr Met Glu Lys Val Thr Ala Met
                325                 330                 335

Gly Val Pro Gln Ile Trp Trp Asp Asn Gly Val Phe Glu Gly Thr Gly
            340                 345                 350
```

-continued

```
Glu Arg Phe Gly Leu Leu Asp Arg Lys Asn Leu Lys Ile Val Tyr Pro
        355                 360                 365

Thr Ile Val Ala Ala Leu Gln Lys Gly Arg Gly Leu Glu Val Asn Val
        370                 375                 380

Val His Ala Ile Glu Lys Glu Thr Glu Glu
385                 390
```

US 6,222,028 B1

POLYNUCLEOTIDES ENCODING CELLULASE ENZYMES FROM *PIROMYCES RHIZINFLATA*

BACKGROUND OF THE INVENTION

Cellulases are enzymes that can hydrolyze the glycosidic linkages in polysaccharides such as cellulose. These enzymes are used in a number of industrial applications where breaking down biomass is beneficial. For example, cellulases can be used as a supplement in animal feed to decrease the production of fecal waste by increasing the digestibility of the feed. Cellulases can also be used to increase the efficiency of alcoholic fermentations (e.g., in beer brewing) by converting undigestible biomass into fermentable sugars. In addition, the "softening" of blue jeans to produce a "stone-washed" look can be facilitated by treating the jeans with cellulases.

SUMMARY OF THE INVENTION

The invention is based on the discovery of a new cellulase isolated from the fungus *Piromyces rhizinflata*. The gene encoding this cellulase is designated eglA. A portion of an eglA cDNA is described below.

Accordingly, the invention features a substantially pure polypeptide having an amino acid sequence at least 70% (e.g., at least 80, 90, or 95%) conserved with or identical to an amino acid sequence representing the catalytic domain of EGLA (SEQ ID NO:4; described below), the polypeptide encoded by eglA. The polypeptide is capable of hydrolyzing a polysaccharide containing a β-1,3' or β-1,4' glycosidic linkage. Such a polysaccharide can be cellulose (e.g., carboxymethyl cellulose), polysaccharides containing both β-1,3' and β-1,4' glycosidic linkage (e.g., barley β-glycan), or lechinan.

The invention also includes an isolated nucleic acid encoding a polypeptide of the invention. For example, the invention includes an isolated nucleic acid having a sequence encoding a polypeptide that hydrolyzes a polysaccharide containing a β1,3' or β1,4' glycosidic linkage, provided that the nucleic acid hybridizes under stringent conditions to SEQ ID NO:1.

In addition, the invention features any vectors or transformed cells which contain a nucleic acid of the invention. Vectors include nucleic acid vectors, such as expression plasmids, or viral vectors. Transformed cells include eukaryotic and prokaryotic cells.

A "nucleic acid" encompasses both RNA and DNA, including cDNA, genomic DNA, and synthetic (e.g., chemically synthesized or modified) DNA. The nucleic acid may be double-stranded or single-stranded. Where single stranded, the nucleic acid may be a sense strand or an antisense strand. An "isolated nucleic acid" refers to a nucleic acid which may be flanked by non-natural sequences, such as those of a plasmid or virus. Thus, the nucleic acid can include none, some, or all of the 5' non-coding (e.g., promoter) sequences which are immediately contiguous to the coding sequence. The term, therefore, includes, for example, a recombinant DNA which is incorporated into a vector including an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. The term also includes a recombinant DNA or RNA which is part of a hybrid gene encoding an additional polypeptide sequence. Moreover, the term is meant to include nucleic acid fragments which are not naturally occurring as fragments and would not be found in the natural state.

By "hybridizes under stringent conditions" is meant specific and non-covalent binding to an immobilized reference nucleic acids in the presence of 0.2×SSC (1.75 g/l NaCl, 0.88 g/l Na$_3$citrate. 2H$_2$O; pH 7.0) and 0.1% (w/v) sodium dodecylsulfate at 68° C.

The term "substantially pure" as used herein in reference to a given polypeptide means that the polypeptide is substantially free from other compounds, such as those in cellular material, viral material, or culture medium, with which the polypeptide may have been associated (e.g., in the course of production by recombinant DNA techniques or before purification from a natural biological source). The polypeptide is at least 75% (e.g., at least 80, 85, 95, or 99%) by weight pure. Purity can be measured by any appropriate standard method, for example, by column chromatography, polyacrylamide gel electrophoresis, or HPLC analysis.

Where a particular polypeptide or nucleic acid molecule is said to have a specific percent identity or conservation to a reference polypeptide or nucleic acid, the percent identity or conservation is determined by the algorithm of Myers and Miller, CABIOS (1989), which is embodied in the ALIGN program (version 2.0), or its equivalent, using a gap length penalty of 12 and a gap penalty of 4 where such parameters are required. All other parameters are set to their default positions. Access to ALIGN is readily available. See, e.g., http://www2.igh.cnrs.fr\/bin/align-guess.cgi on the Internet.

Other features or advantages of the present invention will be apparent from the following detailed description, the drawings, and also from the claims.

DETAILED DESCRIPTION OF THE INVENTION

The invention relates to a cellulase enzyme, nucleic acids encoding it, and vectors and cells containing such nucleic acids. Contemplated within the scope of this invention are recombinant nucleic acids or viruses which allow production of EGLA in a transformed cell or transgenic organism or allow ease of producing specific or non-specific mutations within the EGLA reading frame. These recombinant nucleic acids or viruses may further include any one of a variety of sequences flanking or within the EGLA coding sequences, such as strong constitutive promoters within the EGLA coding sequence, as introns containing cis-elements that allow high level expression, or efficient polyadenylation signals.

Without further elaboration, it is believed that one skilled in the art can, based on the above disclosure and the isolation of EGLA polypeptides and nucleic acids described below, utilize the present invention to its fullest extent. The following examples are to be construed as merely illustrative of how one skilled in the art can isolate and use EGLA polypeptides and nucleic acids from biological sources, and are not limitative of the remainder of the disclosure in any way. For example, once the sequence of the egla cDNA is known, any egla sequence can be obtained by PCR amplification of mRNA or genomic DNA. Any publications cited in this disclosure are hereby incorporated by reference.

The anaerobic fungus *Piromyces rhizinflata*, strain 2301, was cultivated anaerobically at 39° C. in a modified semi-defined medium as described in Lowe et al., J. Gen. Microbiol. 131:2225–2229, 1985. The mycelia were harvested from the culture media, lyophilized, frozen in liquid nitrogen, and ground into a powder. The powder was homogenized in extraction buffer containing 100 mM Tris-HCl (pH 8.0), 50 mM EDTA, 500 mM NaCl, 2% SDS, and 1% β-mercaptoethanol. An equal volume of a 1:1 mixture of phenol/chloroform was added, and the resulting mixture vortexed for 60 seconds and then centrifuged. The aqueous phase was extracted with the phenol/chloroform again. A one-third volume of 8 M LiCl was then added to the extracted mixture. The mixture was centrifuged sufficiently to pellet the RNA, which was washed with 2 M LiCl, followed by 80% ethanol. The washed RNA was then resuspended in diethyl pyrocarbonate (DEPC)-treated water.

Polyadenylated RNA was isolated from total RNA using a standard oligo-(dT)-cellulose chromatography column. The construction of a cDNA expression library was carried out using a Stratagene kit. The library was screened for cellulase activity by overlaying plaques with 0.7% (w/v) agarose containing 0.2% (w/v) carboxymethyl cellulose (CMC). The plates were incubated at 39° C. overnight, then stained with a 0.1% (w/v) aqueous solution of Congo red and destained with 1 M NaCl as described in Teather et al., App. Environ. Microbiol. 43:777–780, 1982. Cellulase-producing plaques were surrounded by a clear halo visible against a red background. The positive clones were excised and purified using standard procedures. One of the clones, designated pPr2301-10, was selected for further study. The mRNA and gene from which the cDNA residing in pPr2301-10 was designated eglA.

The complete sequence of the cDNA insert in plasmid pPr2301-10 was determined using a commercial service (Bio S&T, Lachine, QC, Canada). Translation of one reading frame revealed a 1748 bp open reading frame (ORF), as shown below.

```
   1      GG CAC GAG CTT GAA TGG AAC ATT AAT TTA ATG AAG AAA AGA TTT GTT GAT CAA GGT    56
   1         H   E   L   E   W   N   I   N   L   M   K   K   R   F   V   D   Q   G     18

57     ATT CCA ATG ATT CTT GGT GAA TAT GGT GCT ATG AAC CGT GAC AAT GAA GAA GAT CGT GCT   116
  19      I   P   M   I   L   G   E   Y   G   A   M   N   R   D   N   E   E   D   R   A    38

117     ACT TGG GCT GAA TTC TAC ATG GAA AAG GTT ACT GCT ATG GGA GTT CCA CAA ATC TGG TGG   176
  39      T   W   A   E   F   Y   M   E   K   V   T   A   M   G   V   P   Q   I   W   W    58

177     GAT AAT GGT ATC TTC CAA GGT ACT GGT GAA CGT TTT GGT CTT CTT GAT CGT AAG AAC TTA   236
  59      D   N   G   I   F   Q   G   T   G   E   R   F   G   L   L   D   R   K   N   L    78

237     AAG ATT GTT TAT CCA ACT ATT GTT GCT GCT TTA CAA AAG GGT AGA GGT TTA GAA GTT AAT   296
  79      K   I   V   Y   P   T   I   V   A   A   L   Q   K   G   R   G   L   E   V   N    98

297     GTT GTT CAT GCT GTT GAA AAA AAA CCA GAC GAA CCA ACT AAA ACT ACC AAA CCA ACT GAA   356
  99      V   V   H   A   V   E   K   K   P   D   E   P   T   K   T   T   K   P   T   E   118

357     CCA ACT GAA ACT ACT AGT CCA GAA GAA TCA ACT AAG CCA GAA GAA CCA ACT GGT AAT ATC   416
 119      P   T   E   T   T   S   P   E   E   S   T   K   F   E   E   P   T   G   N   I   138

417     CGT GAT ATT TCA TCA AAG GAA TTG ATT AAG GAA ATG AAT TTC GGT TGG AAT TTA GGT AAT   476
 139      R   D   I   S   S   K   E   L   I   K   E   M   N   F   G   W   N   L   G   N   158

477     ACT ATG GAT GCT CAA TGT ATT GAA TAC TTA AAT TAT GAA AAG GAT CAA ACT GCT TCA GAA   536
 159      T   M   D   A   Q   C   I   E   Y   L   N   Y   E   K   D   Q   T   A   S   E   178

537     ACT TGC TGG GGT AAT CCA AAG ACT ACT GAA GAT ATG TTC AAG GTT TTA ATC GAC AAC CAA   596
 179      T   C   W   G   N   P   K   T   T   E   D   M   F   K   V   L   I   D   N   Q   198

597     TTT AAT GTC TTC CGT ATT CCA ACT ACT TGG TCT GGT CAC TTC GGT GAA GCT CCA GAT TAT   656
 199      F   N   V   F   R   I   P   T   T   W   S   G   H   F   G   E   A   P   D   Y   218

657     AAG ATT GAT GAA AAA TGG TTA AAG AGA GTT CAT GAA GTT GTT GAT TAT CCA TAC AAG AAC   716
 219      K   I   D   E   K   W   L   K   R   V   H   E   V   V   D   Y   P   Y   K   N   238

717     GGA GCA TTT GTT ATC TTA AAT CTT CAT CAT GAA ACC TGG AAT CAT GCC TTC TCT GAA ACT   776
 239      G   A   F   V   I   L   N   L   H   H   E   T   W   N   H   A   F   S   E   T   258

777     CTT GAT ACA GCC AAG GAA ATT TTA GAA AAG ATC TGG TCT CAA ATT GCT GAA GAA TTT AAG   836
 259      L   D   T   A   K   E   I   L   E   K   I   W   S   Q   I   A   E   E   F   K   278

837     GAT TAT GAT GAA CAC TTA ATC TTC GAA GGA TTA AAC GAA CCA AGA AAG AAT GAT ACT CCA   896
 279      D   Y   D   E   H   L   I   F   E   G   L   N   E   P   R   K   N   D   T   P   299

897     GTT GAA TGG ACT GGT GGT GAT CAA GAA GGT TGG GAT GCT GTT AAT GCT ATG AAT GCT GTT   956
 299      V   E   M   T   G   G   D   Q   E   G   W   D   A   V   N   A   M   N   A   V   318

957     TTC TTA AAG ACT GTT CGT AGT GCT GGT GGT AAT AAT CCA AAG CGT CAT CTT ATG ATT CCA  1016
 319      F   L   K   T   V   R   E   A   G   G   N   N   P   K   R   H   L   M   I   P   338

1017     CCA TAT GCT GCT GCT TGT AAT GAA AAC TCA TTC AAC AAC TTT ATC TTC CCA GAA GAT GAT  1076
 339      P   Y   A   A   A   C   N   E   N   S   F   N   N   F   I   F   P   E   D   D   358

1077     GAT AAG GTT ATT GCT TCT GTT CAT GCC TAT GCT CCA TAC AAC TTT GCC TTA AAT AAC GGT  1136
 359      D   K   V   I   A   S   V   H   A   Y   A   P   Y   N   F   A   L   N   N   G   378

1137     GAA GGA GCT GTT GAT AAG TTT GAT GCA GCT GGT AAG AGA GAT CTT GAA TGG AAC ATT AAT  1196
 379      E   G   A   V   D   K   F   D   A   A   G   K   R   D   L   E   W   N   I   N   398
```

-continued

```
1197 TTA ATG AAG AAG AGA TTT GTT GAT CAA GGT ATT CCA ATG ATT CTT GGT GAA TAT GGT GCT 1256
399  L   M   K   K   R   F   V   D   Q   G   I   P   M   I   L   G   E   Y   G   A   418

1257 ATG AAC CGT GAC AAT GAA GAA GAT CGT GCT ACT TGG GCT GAA TTC TAC ATG GAA AAG GTT 1316
419  M   N   R   D   N   E   E   D   R   A   T   W   A   E   F   Y   M   E   K   V   438

1317 ACT GCT ATG GGA GTT CCA CAA ATC TGG TGG GAT AAT GGT GTC TTC GAA GGT ACT GGT GAA 1376
439  T   A   M   G   V   P   Q   I   W   W   D   N   G   V   F   E   G   T   G   E   458

1337 CGT TTT GGT CTT CTT GAT CGT AAG AAC TTA AAG ATT GTT TAT CCA ACT ATT GTT GCT GCT 1436
459  R   F   G   L   L   D   R   K   N   L   K   R   V   Y   P   T   I   V   A   A   478

1437 TTA CAA AAG GGT AGA GGT TTA GAA GTT AAT GTT GTT CAT GCT ATT GAA AAA GAA ACA GAG 1496
479  L   Q   K   G   R   G   L   E   V   N   V   V   H   A   I   E   K   E   T   E   498

1497 GAA TGT TGG TCC GAA AAG TAT GGT TAT GAA TGT TGT TCA CCA AAC AAT ACT AAG GTT GTA 155
499  E   C   W   S   E   K   Y   G   Y   E   C   C   S   P   N   N   T   K   V   V   518

1557 GTC AGT GAT GAA AGT GGT AAA TGG GGT GTT GAA AAT GGT AAC TGG TGT GGT GTA CTC AAA 116
519  V   S   D   E   S   G   K   W   G   V   E   N   G   N   W   C   G   V   L   K   538

1617 TAC ACT GAA ACT TGT TGG TCA CTT CCA TTT GGA TAC CCA TGT TGT CCA CAT TGT AAG GCT 1676
539  Y   T   E   T   C   W   S   L   P   F   G   Y   P   C   C   P   H   C   K   A   538

1677 CTT ACT AAG GAT GAG AAT GGT AAA TGG GGA GAA TTA AAT GGA GAA TGG TAT GGT ATT GTT 173
559  L   T   K   D   E   N   G   K   W   G   E   L   N   G   E   W   Y   G   I   V   578

1737 GCT GAT AAA TGT TAA attataaaataagaataaataaatttctaatgaaaaattatttaaaaaaaaataaaatag 1811
579  A   D   K   C   *                                                                582

1812 aaaaatttatatacacatatttctaataaaatgtcatttaaaatttttatttcttattattttttaataaaaaaaattata 1891

1892 agaaaagaaaatataaaaaataataataatgaatgaaataaaattttaattatttattcttttacttaaagcaaaaaaaa 1971

1972 gaatttaattaaaatcaagaattttttaaagatggaatatgtattttaaataatagctaataagattataaaaattgtgta 2051

2052 aaaaattttaaataaaataaaaataaaataaataaataaataaataaaaaaaaaataa                        2110
```

This partial cDNA sequence (SEQ ID NO:1) of an eglA from *Piromyces rhizinflata* encodes the partial EGLA amino acid sequence (SEQ ID NO:2) shown immediately above. Analysis of the amino acid sequence encoded by the ORF indicated two nearly identical repeats, which are aligned as follows.

```
  1 HELEWNINLMKKRFVDQGIPMILGEYGAMNRDNEEDRATWAEFYMEKVTA  50
391 RDLEWNINLMKKRFVDQGIPMILGEYGAMNRDNEEDRATWAEFYMEKVTA 440

51 MGVPQIWWDNGIFQGTGERFGLLDRKNLKIVYPTIVAALQKGRGLEVNVV 100
441 MGVPQIWWDNGVFEGTGERFGLLDRKNLKIVYPTIVAALQKGRGLEVNVV 490

101 HAVEKKPDE      109
491 HAIEKETEE      499
```

The two regions are amino acids 1–109 (SEQ ID NO:5) and 391–499 (SEQ ID NO:6) of EGLA. The bolded sequences in the two regions indicate identical amino acids in the alignment. It was noted that such repeats are one of the characteristics 10 of many cellulase genes (see, e.g. Aylward et al., Enzyme Microb. Technol. 24:609–614, 1999). No translation initiation codon was found at the 5' end, suggesting that the cDNA is incomplete. Using previously known cellulase genes as a model, the cDNA of pPr2301-10 clone appeared to be missing a N-terminal catalytic domain but includes a complete C-terminal catalytic domain. Based on this assumption, amino acids 110–499 of the above polypeptide sequence was considered to be a catalytic domain of EGLA and was further characterized.

The nucleic acid sequence encoding the putative EGLA catalytic domain was amplified by PCR using primers 10F (GCA<u>GGATCC</u>ATTATGGAGCTCCCAACTAAAACTAC CAAACCA; SEQ ID NO:7) and 10R (TTCC<u>TCGAG</u>T TAGAGCTCTTCCTCTGTTTCTTTTTCAAT; SEQ ID NO:8). To facilitate cloning, 10F contains a BamHI site, while 10R contains a XhoI site; both restriction sites are underlined in the primer sequences immediately above. The PCR product was then digested with the appropriate enzymes and ligated into BamHI and XhoI digested pGEX-4T-3 (Pharmacia Biotech, Inc.) to produce the Glutathione S-transferase (GST)-fusion expression plasmid pGEX-EGLA. The amino acid sequence downstream of the GST is shown below.

```
  1 ATT ATG GAG CTC CCA ACT AAA ACT ACC AAA CCA ACT GAA CCA ACT GAA ACT ACT AGT CCA  60
  1  I   M   E   L   P   T   K   T   T   K   P   T   E   P   T   E   T   T   S   P   19

61 GAA GAA TCA ACT AAG CCA GAA GAA CCA ACT GGT AAT ATC CGT GAT ATT TCA TCA AAG GAA 120
 20  E   E   S   T   K   P   E   E   P   T   G   N   Z   R   D   I   S   S   K   E   39

121 TTG ATT AAG GAA ATG AAT TTC GGT TGG AAT TTA GGT AAT ACT ATG GAT GCT CAA TGT ATT 180
 40  L   I   K   E   M   N   F   G   W   N   L   G   N   T   M   D   A   Q   C   I   59

181 GAA TAC TTA AAT TAT GAA AAG GAT CAA ACT GCT TCA GAA ACT TGC TGG GGT AAT CCA AAG 240
 60  E   Y   L   N   Y   E   K   D   Q   T   A   S   E   T   C   W   G   N   P   K   79

241 ACT ACT GAA GAT ATG TTC AAG GTT TTA ATC GAC AAC CAA TTT AAT GTC TTC CGT ATT CCA 300
 80  T   T   E   D   M   F   K   V   L   I   D   N   Q   F   N   V   F   R   I   P   99

301 ACT ACT TGG TCT GGT CAC TTC GGT GAA GCT CCA GAT TAT AAG ATT GAT GAA AAA TGG TTA 360
100  T   T   W   S   G   N   F   G   E   A   P   D   Y   K   I   D   E   K   W   L  119

361 AAG AGA GTT CAT GAA GTT GTT GAT TAT CCA TAC AAG AAC GGA GCA TTT GTT ATC TTA AAT 420
120  K   R   V   H   E   V   V   D   Y   P   Y   K   N   G   A   F   V   I   L   N  139

421 CTT CAT CAT GAA ACC TGG AAT CAT GCC TTC TCT GAA ACT CTT GAT ACA GCC AAG GAA ATT 480
140  L   H   H   E   T   W   N   H   A   F   S   E   T   L   D   T   A   K   E   I  159

481 TTA GAA AAG ATC TGG TCT CAA ATT GCT GAA GAA TTT AAG GAT TAT GAT GAA CAC TTA ATC 540
160  L   E   K   I   W   S   Q   I   A   E   E   F   K   D   Y   D   E   H   L   I  179

541 TTC GAA GGA TTA AAC GAA CCA AGA AAG AAT GAT ACT CCA GTT GAA TGG ACT GGT GGT GAT 600
180  F   E   G   L   N   E   P   R   K   N   D   T   P   V   E   W   T   G   G   D  199

601 CAA GAA GGT TGG GAT GCT GTT AAT GCT ATG AAT GCT GTT TTC TTA AAG ACT GTT CGT AGT 660
200  Q   E   G   W   D   A   V   N   A   M   N   A   V   F   L   K   T   V   R   S  219

661 GCT GGT GGT AAT AAT CCA AAG CGT CAT CTT ATG ATT CCA CCA TAT GCT GCT GCT TGT AAT 720
220  A   G   G   N   N   P   K   R   H   L   M   I   P   P   Y   A   A   A   C   N  239

721 GAA AAC TCA TTC AAC AAC TTT ATC TTC CCA GAA GAT GAT GAT AAG GTT ATT GCT TCT GTT 780
240  E   N   S   F   N   N   F   I   F   P   E   D   D   D   K   V   I   A   S   V  259

761 CAT GCC TAT GCT CCA TAC AAC TTT GCC TTA AAT AAC GGT GAA GGA GCT GTT GAT AAG TTT 840
260  H   A   Y   A   P   Y   N   F   A   L   N   N   G   E   G   A   V   D   K   F  279

841 GAT GCA GCT GGT AAG AGA GAT CTT GAA TGG AAC ATT AAT TTA ATG AAG AAG AGA TTT GTT 900
280  D   A   A   G   K   R   D   L   E   W   N   I   N   L   M   K   K   R   F   V  299

901 GAT CAA GGT ATT CCA ATG ATT CTT GGT GAA TAT GGT GCT ATG AAC CGT GAC AAT GAA GAA 960
300  D   Q   G   I   P   M   I   L   G   E   Y   G   A   M   N   R   D   N   E   E  319

961 GAT CGT GCT ACT TGG GCT GAA TTC TAC ATG GAA AAG GTT ACT GCT ATG GGA GTT CCA CAA 1020
320  D   R   A   T   W   A   E   F   Y   M   E   K   V   T   A   M   G   V   P   Q  339

1021 ATC TGG TGG GAT AAT GGT GTC TTC GAA GGT ACT GGT GAA CGT TTT GGT CTT CTT GAT CGT 1080
340  I   W   W   D   N   G   V   F   E   G   T   G   E   R   F   G   L   L   D   R  359

1081 AAG AAC TTA AAG ATT GTT TAT CCA ACT ATT GTT GCT GCT TTA CAA AAG GGT AGA GGT TTA 1140
360  K   N   L   K   I   V   Y   P   T   I   V   A   A   L   Q   K   G   R   G   L  379

1141 GAA GTT AAT GTT GTT CAT GCT ATT GAA AAA GAA ACA GAG GAA                          1182
380  E   V   N   V   V   H   A   I   E   K   E   T   E   E                            393
```

The complete nucleic acid sequence immediately above is designated SEQ ID NO:9, and the complete amino acid sequence encoded by that nucleic acid sequence is designated SEQ ID NO:10. Nucleotides 13–1182 of SEQ ID NO:9 (SEQ ID NO:3) correspond to nucleotides 331–1499 of SEQ ID NO:1. Amino acids 5–393 of SEQ ID NO:10 (SEQ ID NO:4) correspond to amino acids 110–499 of SEQ ID NO2.

The EGLA catalytic domain expression plasmid was used to transformed *E. coli* to produce recombinant EGLA. GST-EGLA was purified on glutathione Sepharose 4B (Pharmacia Biotech, Inc.) following the manufacturer's protocols. Bound fusion protein was cleaved with thrombin to release only the EGLA catalytic domain.

The enzymatic activity of the EGLA fragment was determined as follows. The purified protein was suspended in 50 mM sodium phosphate buffer containing 1% CMC, 1% oat spelt xylan, 0.4% barley β-glucan, 1% lechinan, 5 mM pNP-β-D-glucoside, Avicel, or 5 mM pNP-β-D-cellobioside. The barley β-glucan contains mixed β-1,3'–1,4' glucan. Enzymatic activity was measured by detecting the amount of reducing sugar released from the substrate. After incubating the reaction at 50° C. for 10 minutes, the reaction was stopped by adding a half-volume each of 0.3% (w/v) 3,6-dinitrophthalic acid and stop solution (25% $K_2CO_3$ and 5% $Na_2S_2O_3$). The stopped reaction was then boiled for 10 minutes before absorbance at 450 nm was read. Protein concentrations were measured using a protein assay kit (BioRad). The results are summarized in Table 1 below.

TABLE 1

| Substrate | Specific Activity (μmoles glucose/mg/min) | Relative Activity (%) |
|---|---|---|
| Carboxymethyl cellulose | 590.8 | 100 |
| Barley β-glucan | 745.7 | 126.2 |
| Lechinan | 565.7 | 95.8 |
| Oat Spelt Xylan | 127.6 | 21.6 |

No activity was detected using pNP-β-D-glucoside, Avicel, or pNP-β-D-cellobioside as a substrate under these conditions.

Using the assay described immediately above, the temperature or pH was varied to obtain conditions necessary for optimal activity. The optimal temperature for the EGLA catalytic domain was about 50° C., and the optimal pH for the catalytic domain was about 5.5. In addition, EGLA retained about 30% activity against the substrate carboxymethyl cellulose and 42% activity against the substrate barley β-glucan after the enzyme was heated to 80° C. for 10 min, indicating that the EGLA catalytic domain described here is moderately heat stable.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. An isolated nucleic acid encoding a polypeptide, the amino acid sequence of which is at least 95% identical to SEQ ID NO:4, wherein said polypeptide hydrolyzes a polysaccharide containing a β-1,3' or β-1,4' glycosidic linkage.

2. The isolated nucleic acid of claim 1 encoding a polypeptide, the amino acid sequence of which is SEQ ID NO:4.

3. The isolated nucleic acid of claim 2, wherein the nucleic acid sequence is SEQ ID NO:3.

* * * * *